United States Patent
Accisano, III

(10) Patent No.: US 12,226,327 B2
(45) Date of Patent: Feb. 18, 2025

(54) SYSTEMS AND METHODS FOR COUPLING AND DECOUPLING A CATHETER

(71) Applicant: Merit Medical Systems, Inc., South Jordan, UT (US)

(72) Inventor: Nicholas Accisano, III, Howell, NJ (US)

(73) Assignee: Merit Medical Systems, Inc., South Jordan, UT (US)

( * ) Notice: Subject to any disclaimer, the term of this patent is extended or adjusted under 35 U.S.C. 154(b) by 894 days.

(21) Appl. No.: 17/226,839

(22) Filed: Apr. 9, 2021

(65) Prior Publication Data

US 2021/0322190 A1    Oct. 21, 2021

Related U.S. Application Data

(60) Provisional application No. 63/010,521, filed on Apr. 15, 2020.

(51) Int. Cl.
*A61F 2/95* (2013.01)
*A61M 27/00* (2006.01)

(52) U.S. Cl.
CPC .............. *A61F 2/95* (2013.01); *A61M 27/002* (2013.01); *A61F 2002/9505* (2013.01); *A61F 2220/0033* (2013.01); *A61F 2250/0065* (2013.01)

(58) Field of Classification Search
CPC ......... A61M 2025/0175; A61M 27/002; A61F 2/04; A61F 2/95; A61F 2/9517; A61F 2002/048; A61F 2002/9505; A61F 2220/0033; A61F 2250/0065; A61F 2250/0098

See application file for complete search history.

(56) References Cited

U.S. PATENT DOCUMENTS

| | | | |
|---|---|---|---|
| 818,817 | A | 4/1906 | Leva |
| 3,996,938 | A | 12/1976 | Clark, III |
| 4,350,161 | A | 9/1982 | Davis, Jr. |
| 4,790,810 | A | 12/1988 | Pugh, Jr. et al. |
| 4,813,925 | A | 3/1989 | Anderson, Jr. et al. |

(Continued)

FOREIGN PATENT DOCUMENTS

| | | |
|---|---|---|
| CN | 2128148 | 3/1993 |
| CN | 2408894 | 12/2000 |

(Continued)

OTHER PUBLICATIONS

Office Action dated Feb. 10, 2022 for U.S. Appl. No. 15/901,833.

(Continued)

*Primary Examiner* — Kai H Weng
(74) *Attorney, Agent, or Firm* — Dorsey & Whitney LLP

(57) ABSTRACT

A drainage stent delivery system is disclosed. The system can include a catheter body, a stent member, and a coupling member. The coupling member is configured to selectively couple and decouple the catheter body and the stent member. The coupling member can include a first connector, a second connector, and a telescoping connector. A tab of the first connector is configured to be received by a slot of the second connector when the first and second connectors are coupled. The telescoping connector can displace the tab radially outward to be received by the slot. The tab is biased radially inward when the telescoping connector is displaced. When coupled, the catheter body and the stent member are rotationally fixed.

14 Claims, 6 Drawing Sheets

(56) References Cited

U.S. PATENT DOCUMENTS

| | | |
|---|---|---|
| 4,830,003 A | 5/1989 | Wolff et al. |
| 4,913,683 A | 4/1990 | Gregory |
| 4,957,479 A | 9/1990 | Roemer |
| 4,963,129 A | 10/1990 | Rusch |
| 5,002,560 A | 3/1991 | Machold et al. |
| 5,019,090 A | 5/1991 | Pinchuk |
| 5,071,407 A | 12/1991 | Termin et al. |
| 5,122,136 A | 6/1992 | Guglielmi |
| 5,221,253 A | 6/1993 | Coll |
| 5,250,069 A | 10/1993 | Nobuyoshi et al. |
| 5,259,847 A | 11/1993 | Trambert |
| 5,282,784 A | 2/1994 | Willard |
| 5,354,263 A | 10/1994 | Coll |
| 5,364,340 A | 11/1994 | Coll |
| 5,456,667 A | 10/1995 | Ham et al. |
| 5,507,732 A | 4/1996 | McClure et al. |
| 5,507,751 A | 4/1996 | Goode et al. |
| 5,599,291 A | 2/1997 | Balbierz et al. |
| 5,643,254 A | 7/1997 | Scheldrup et al. |
| 5,653,684 A | 8/1997 | Laptewicz et al. |
| 5,846,251 A | 12/1998 | Hart |
| 5,876,417 A | 3/1999 | Devonec et al. |
| 5,921,952 A | 7/1999 | Desmond, III et al. |
| 5,964,771 A | 10/1999 | Beyar et al. |
| 6,074,339 A | 6/2000 | Gambale et al. |
| 6,196,996 B1 | 3/2001 | Teirstein |
| 6,248,100 B1 | 6/2001 | De Toledo et al. |
| 6,264,624 B1 | 7/2001 | Desmond, III et al. |
| 6,319,287 B1 | 11/2001 | Frimberger |
| 6,562,024 B2 | 5/2003 | De Toledo et al. |
| 6,569,150 B2 | 5/2003 | Teague et al. |
| 6,576,008 B2 | 6/2003 | Devonec et al. |
| 6,629,981 B2 | 10/2003 | Dennis et al. |
| 6,673,106 B2 | 1/2004 | Mitelberg et al. |
| 6,676,651 B2 | 1/2004 | Haacke et al. |
| 6,913,625 B2 | 7/2005 | Segura et al. |
| 6,929,664 B2 | 8/2005 | Kolb et al. |
| 6,949,125 B2 | 9/2005 | Robertson |
| 6,991,614 B2 | 1/2006 | McWeeney et al. |
| 7,044,980 B2 | 5/2006 | Hammond et al. |
| 7,044,981 B2 | 5/2006 | Liu et al. |
| 7,169,139 B2 | 1/2007 | Teague et al. |
| 7,217,250 B2 | 5/2007 | Kolb et al. |
| 7,367,987 B2 | 5/2008 | Balgobin et al. |
| 7,371,252 B2 | 5/2008 | Balgobin et al. |
| 7,377,932 B2 | 5/2008 | Mitelberg et al. |
| 7,550,002 B2 | 6/2009 | Goto et al. |
| 7,566,316 B2 | 7/2009 | McGuckin, Jr. et al. |
| 7,722,604 B2 | 5/2010 | Brown, III et al. |
| 7,731,676 B2 | 6/2010 | Maeda |
| 7,811,305 B2 | 10/2010 | Balgobin et al. |
| 7,824,367 B2 | 11/2010 | Accisano, III |
| 7,901,704 B2 | 3/2011 | Richard |
| 7,901,444 B2 | 5/2011 | Slazas |
| 7,993,329 B2 | 8/2011 | Howell et al. |
| 8,007,540 B2 | 8/2011 | Robertson |
| 8,021,434 B2 | 9/2011 | Segura et al. |
| 8,034,094 B2 | 10/2011 | Aoba et al. |
| 8,070,825 B2 | 12/2011 | Devonec |
| 8,298,276 B2 | 10/2012 | Ozawa et al. |
| 8,333,000 B2 | 12/2012 | Huang et al. |
| 8,333,796 B2 | 12/2012 | Tompkins et al. |
| 8,603,185 B2 | 12/2013 | Shah et al. |
| 8,657,884 B2 | 2/2014 | Smouse |
| 8,676,349 B2 | 3/2014 | Stalker et al. |
| 8,702,784 B2 | 4/2014 | Weisman et al. |
| 8,753,303 B2 | 6/2014 | Weisman et al. |
| 8,771,335 B2 | 7/2014 | Griego et al. |
| 8,961,518 B2 | 2/2015 | Taylor et al. |
| 8,961,581 B2 | 2/2015 | Taylor et al. |
| 8,979,824 B2 | 3/2015 | Amos et al. |
| 8,986,364 B2 | 3/2015 | Okuma |
| 9,026,229 B2 | 5/2015 | Stalker et al. |
| 9,186,151 B2 | 11/2015 | Tompkins et al. |
| 9,265,637 B2 | 2/2016 | Weisman et al. |
| 9,308,359 B2 | 4/2016 | Ward |
| 9,314,359 B2 | 4/2016 | Windheuser et al. |
| 9,387,312 B2 | 7/2016 | Smouse et al. |
| 9,510,962 B2 | 12/2016 | Aoba et al. |
| 9,517,120 B2 | 12/2016 | Devonec et al. |
| 9,597,207 B2 | 3/2017 | Weisman et al. |
| 9,956,100 B2 | 5/2018 | Smouse et al. |
| 10,310,098 B1 | 6/2019 | Qiang et al. |
| 2002/0055767 A1 | 5/2002 | Forde et al. |
| 2003/0069533 A1 | 4/2003 | Kakutani et al. |
| 2003/0163204 A1 | 8/2003 | Rix |
| 2003/0191450 A1 | 10/2003 | Teague et al. |
| 2003/0195456 A1 | 10/2003 | Robertson |
| 2004/0073283 A1 | 4/2004 | Ewers |
| 2004/0098105 A1 | 5/2004 | Stinson et al. |
| 2004/0181186 A1 | 9/2004 | Gellman et al. |
| 2004/0249343 A1 | 12/2004 | Cioanta |
| 2005/0085892 A1 | 4/2005 | Goto et al. |
| 2007/0078446 A1 | 4/2007 | Lavelle et al. |
| 2007/0112420 A1 | 5/2007 | Laduca |
| 2007/0219612 A1 | 9/2007 | Andreas et al. |
| 2007/0233223 A1 | 10/2007 | Styrc et al. |
| 2007/0276466 A1 | 11/2007 | Lavelle et al. |
| 2008/0109059 A1 | 5/2008 | Gordon et al. |
| 2008/0140101 A1 | 6/2008 | Carley |
| 2008/0221554 A1 | 9/2008 | O'Connor et al. |
| 2009/0048654 A1 | 2/2009 | Chmura et al. |
| 2009/0088833 A1 | 4/2009 | Soetermans |
| 2009/0099640 A1 | 4/2009 | Weng |
| 2009/0105719 A1 | 4/2009 | Honey et al. |
| 2009/0248169 A1 | 10/2009 | Li |
| 2009/0312829 A1 | 12/2009 | Aoba et al. |
| 2010/0070047 A1 | 3/2010 | Smouse |
| 2010/0182271 A1 | 7/2010 | Krier |
| 2010/0185271 A1 | 7/2010 | Zhang |
| 2010/0268201 A1 | 10/2010 | Tieu et al. |
| 2011/0009950 A1 | 1/2011 | Grandfield et al. |
| 2011/0071621 A1 | 3/2011 | Griego et al. |
| 2011/0077622 A1 | 3/2011 | Weisman et al. |
| 2011/0130821 A1 | 6/2011 | Styrc |
| 2011/0190862 A1 | 8/2011 | Bashiri et al. |
| 2011/0196410 A1 | 8/2011 | Besselink et al. |
| 2011/0196507 A1 | 8/2011 | St. Pierre |
| 2011/0282249 A1 | 11/2011 | Tsoref et al. |
| 2011/0282429 A1 | 11/2011 | Shin et al. |
| 2011/0288624 A1 | 11/2011 | Roeder et al. |
| 2011/0295265 A1 | 12/2011 | Hollett et al. |
| 2011/0313404 A1 | 12/2011 | Amos et al. |
| 2012/0041538 A1 | 2/2012 | White et al. |
| 2012/0095567 A1 | 4/2012 | Weisman et al. |
| 2012/0203325 A1 | 8/2012 | Weisman et al. |
| 2012/0330397 A1 | 12/2012 | Harrison et al. |
| 2013/0110042 A1 | 5/2013 | Humphreys et al. |
| 2013/0204344 A1 | 8/2013 | Tatalovich et al. |
| 2013/0254751 A1 | 9/2013 | Phung et al. |
| 2014/0114431 A1 | 4/2014 | Yamagata |
| 2014/0135941 A1 | 5/2014 | Smouse et al. |
| 2014/0172065 A1 | 6/2014 | Lavelle et al. |
| 2014/0194970 A1 | 7/2014 | Chobotov |
| 2014/0200462 A1 | 7/2014 | Stalker et al. |
| 2014/0309721 A1 | 10/2014 | Griego et al. |
| 2015/0005864 A1 | 1/2015 | Okuma |
| 2015/0073525 A1 | 3/2015 | Aoba et al. |
| 2015/0157480 A1 | 6/2015 | Amos et al. |
| 2015/0223953 A1 | 8/2015 | Pendleton et al. |
| 2016/0015509 A1 | 1/2016 | McDonough |
| 2016/0045347 A1 | 2/2016 | Smouse et al. |
| 2016/0120675 A1 | 5/2016 | Weisman et al. |
| 2016/0135941 A1 | 5/2016 | Binmoeller et al. |
| 2016/0151615 A1 | 6/2016 | Overtoom |
| 2016/0184123 A1 | 6/2016 | Windheuser et al. |
| 2016/0287372 A1 | 10/2016 | Smouse et al. |
| 2016/0361167 A1 | 12/2016 | Tuval et al. |
| 2018/0325709 A1 | 11/2018 | Tatalovich et al. |
| 2021/0007870 A1 | 1/2021 | Smouse et al. |

(56) References Cited

U.S. PATENT DOCUMENTS

| | | |
|---|---|---|
| 2021/0322190 A1 | 10/2021 | Accisano, III |
| 2021/0378850 A1 | 12/2021 | Accisano, III |

FOREIGN PATENT DOCUMENTS

| | | |
|---|---|---|
| CN | 201624817 | 11/2010 |
| CN | 102548505 | 7/2012 |
| CN | 102579171 | 7/2012 |
| CN | 102596083 | 7/2012 |
| CN | 202537720 | 11/2012 |
| CN | 202637201 | 1/2013 |
| CN | 103211671 | 7/2013 |
| CN | 103876872 | 6/2014 |
| CN | 103961194 | 8/2014 |
| EP | 0806189 A1 | 11/1997 |
| JP | 2002071765 | 3/2002 |
| JP | 2003530165 | 10/2003 |
| JP | 2009297502 | 12/2009 |
| JP | 2012239803 | 12/2012 |
| JP | 2015073547 | 4/2015 |
| WO | 198805317 | 7/1988 |
| WO | 199611721 | 4/1996 |
| WO | 2013003450 | 1/2013 |
| WO | 2015108609 | 7/2015 |
| WO | 2016025434 | 2/2016 |
| WO | 2016042150 | 3/2016 |
| WO | 2018156650 | 8/2018 |

OTHER PUBLICATIONS

Final Office Action dated Mar. 4, 2022 received in U.S. Appl. No. 15/958,406 (10 pages).
International Search Report and Written Opinion dated Jul. 26, 2021 for PCT/US2021/026886.
Office Action dated May 26, 2022 for U.S. Appl. No. 15/901,833.
Office Action dated Sep. 19, 2019 for U.S. Appl. No. 15/901,833.
Office Action dated Apr. 21, 2021 for U.S. Appl. No. 15/958,406.
Office Action dated May 28, 2021 for U.S. Appl. No. 15/901,833.
Office Action dated Aug. 17, 2021 for U.S. Appl. No. 15/958,406.
Extended European Search Report dated Dec. 9, 2021 for EP21191048.4.
Office Action dated Mar. 4, 2022 for U.S. Appl. No. 15/958,406.
European Search Report dated May 19, 2020 for EP15831895.6.
European Search Report dated Sep. 7, 2017 for EP14878890.4.
European Search Report dated Dec. 22, 2017 for EP15831895.6.
European Search Report dated Dec. 22, 2020 for EP18758123.6.
International Search Report and Written Opinion dated Jan. 7, 2016 for PCT/US2015/44580.
International Search Report and Written Opinion dated Mar. 25, 2015 for PCT/US2014/063758.
International Search Report and Written Opinion dated Jun. 15, 2018 for PCT/US2018/19045.
Notice of Allowance dated Jan. 16, 2018 for U.S. Appl. No. 14/823,243.
Notice of Allowance dated Mar. 26, 2018 for U.S. Appl. No. 14/823,243.
Notice of Allowance dated Apr. 20, 2020 for U.S. Appl. No. 15/936,856.
Notice of Allowance dated Apr. 27, 2020 for U.S. Appl. No. 15/175,436.
Notice of Allowance dated May 13, 2016 for U.S. Appl. No. 14/159,221.
Notice of Allowance dated Oct. 9, 2013 for U.S. Appl. No. 12/559,946.
Office Action dated Jan. 3, 2012 for U.S. Appl. No. 12/559,946.
Office Action dated Jan. 10, 2020 for U.S. Appl. No. 15/936,856.
Office Action dated Feb. 5, 2021 for U.S. Appl. No. 15/901,833.
Office Action dated Feb. 12, 2020 for U.S. Appl. No. 15/901,833.
Office Action dated Feb. 26, 2016 for U.S. Appl. No. 14/159,221.
Office Action dated Apr. 18, 2017 for U.S. Appl. No. 14/823,243.
Office Action dated Apr. 22, 2020 for U.S. Appl. No. 15/958,406.
Office Action dated Aug. 7, 2020 for U.S. Appl. No. 15/958,406.
Office Action dated Aug. 31, 2017 for U.S. Appl. No. 14/823,243.
Office Action dated Sep. 4, 2020 for U.S. Appl. No. 15/901,833.
Office Action dated Sep. 9, 2019 for U.S. Appl. No. 15/175,436.
Office Action dated Oct. 7, 2015 for U.S. Appl. No. 14/159,221.
Office Action dated Oct. 21, 2019 for U.S. Appl. No. 15/958,406.
Office Action dated Oct. 24, 2012 for U.S. Appl. No. 12/559,946.
Office Action dated Dec. 31, 2019 for U.S. Appl. No. 15/175,436.
Notice of Allowance dated Nov. 8, 2023 for U.S. Appl. No. 16/937,280.
Office Action dated Jan. 12, 2023 for U.S. Appl. No. 15/901,833.
European Search Report dated May 31, 2024 for EP21818001.6.
Extended European Search Report dated May 3, 2024 for EP21788557.3.

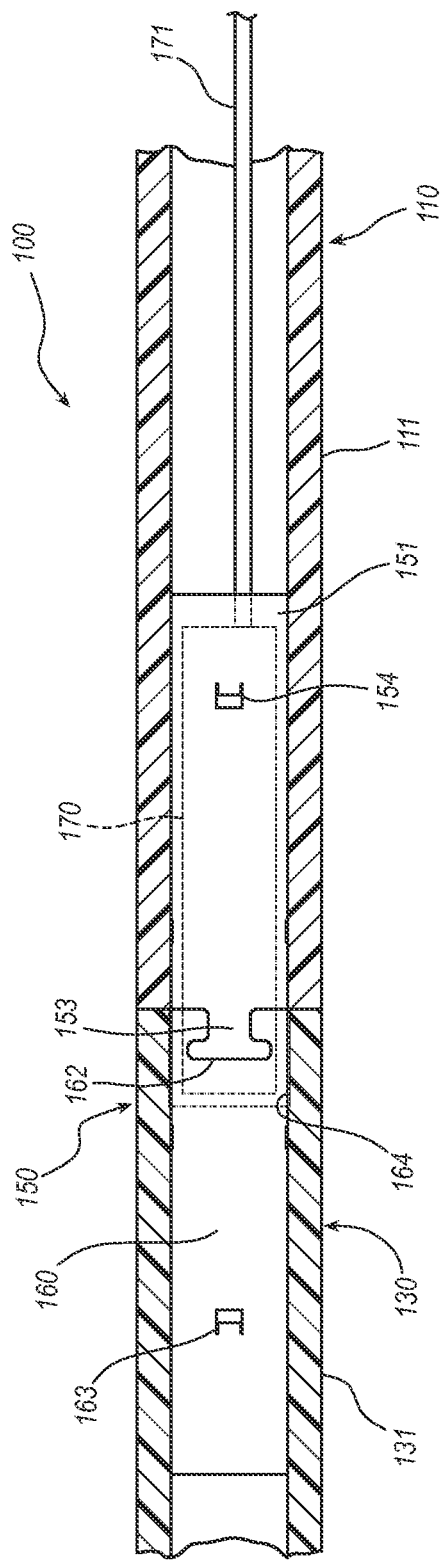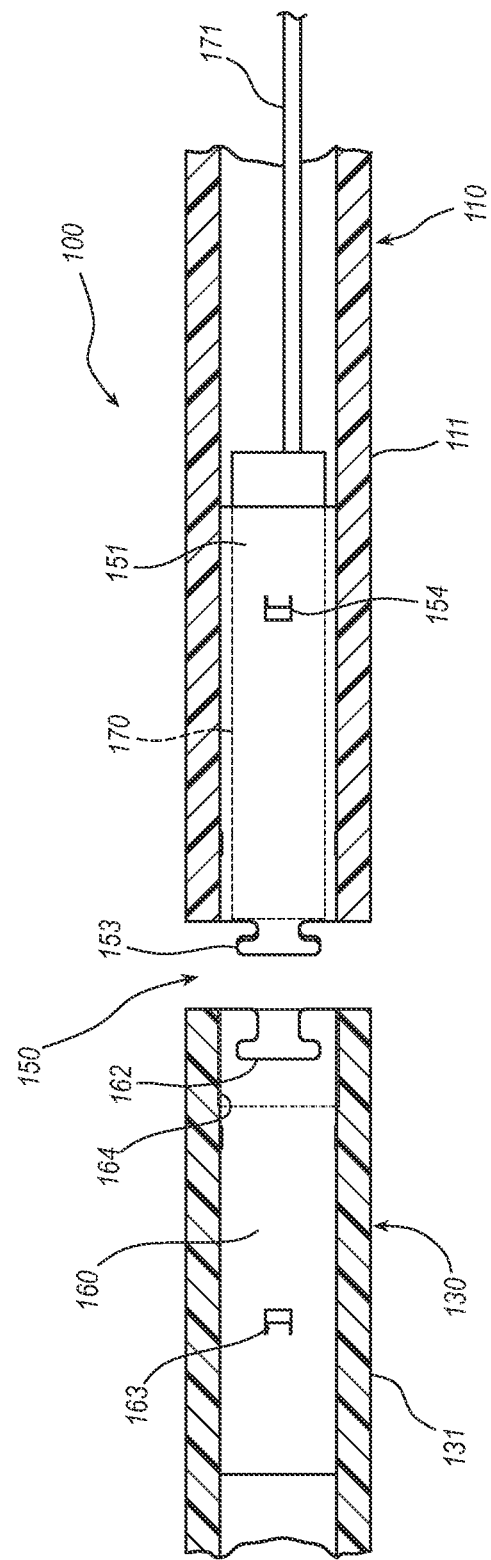
FIG. 4A
FIG. 4B

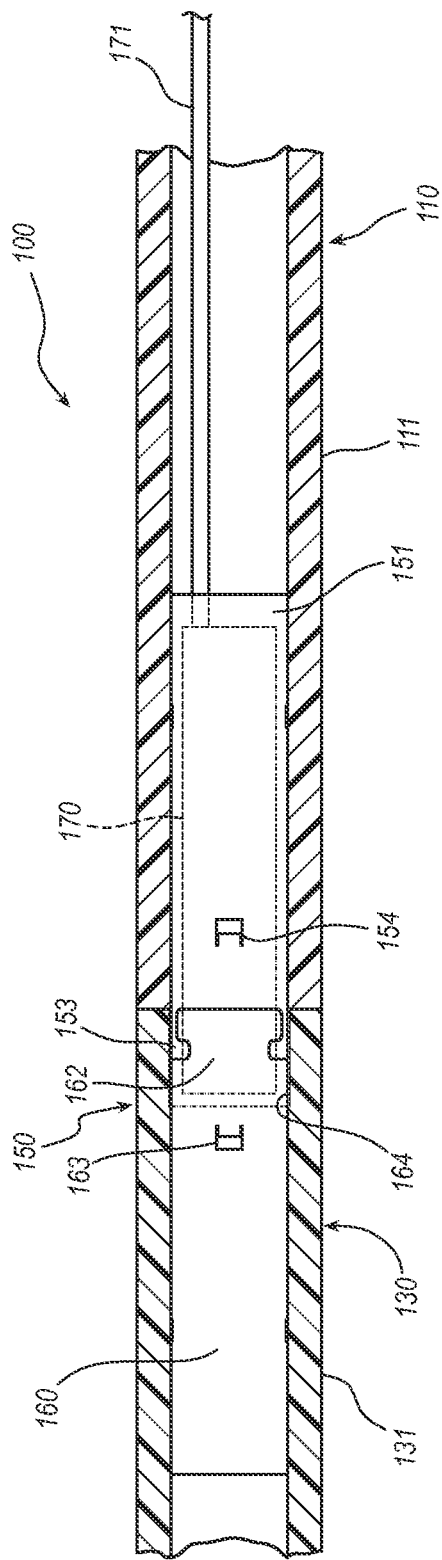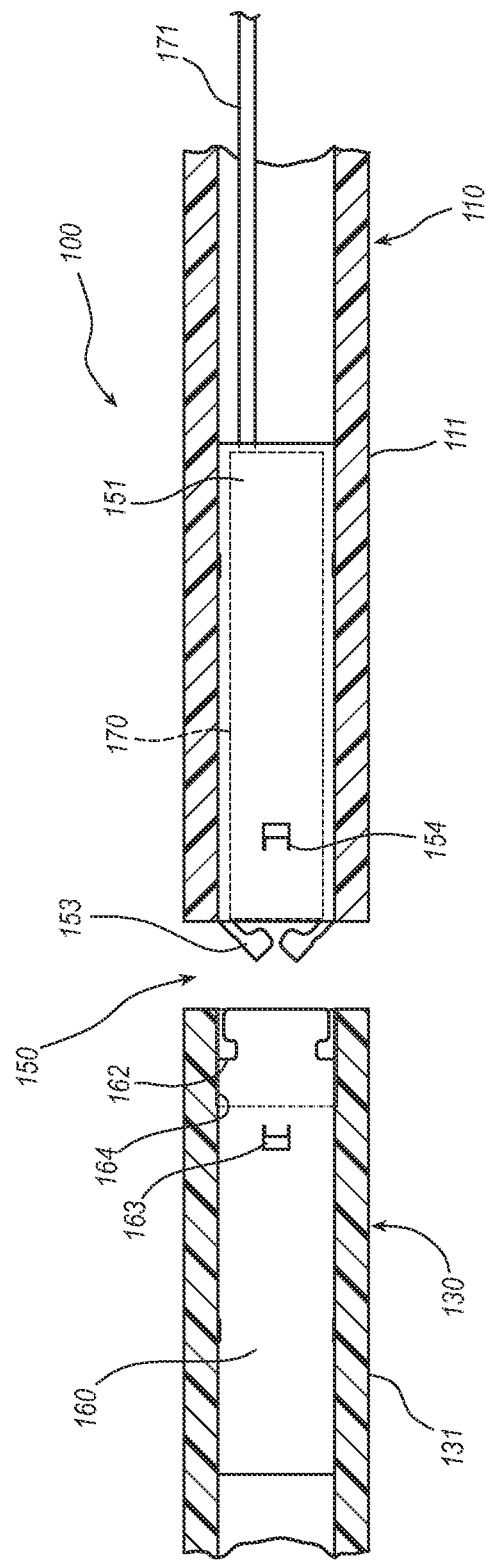

SYSTEMS AND METHODS FOR COUPLING AND DECOUPLING A CATHETER

CROSS-REFERENCE TO RELATED APPLICATIONS

This application claims priority to U.S. Provisional Application No. 63/010,521, filed Apr. 15, 2020, and titled SYSTEMS AND METHODS FOR COUPLING AND DECOUPLING A CATHETER, which is hereby incorporated by reference in its entirety.

TECHNICAL FIELD

The present disclosure relates generally to devices and methods to selectively couple tubular members, particularly in medical devices. More specifically, the present disclosure relates to drainage stent delivery systems comprising a catheter and a stent that can be percutaneously inserted into a patient, after which the stent can be remotely decoupled from the catheter.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 4A is a partial cutaway side view of a portion of the drainage stent delivery system of FIG. 1 in a coupled configuration.

FIG. 4B is a partial cutaway side view of a portion of the drainage stent delivery system of FIG. 1 in a decoupled configuration.

FIG. 5A is a partial cutaway side view of the portion of the drainage stent delivery system of FIG. 4A rotated 90 degrees.

FIG. 5B is a partial cutaway side view of the portion of the drainage stent delivery system of FIG. 4B rotated 90 degrees.

DETAILED DESCRIPTION

Figure 1:
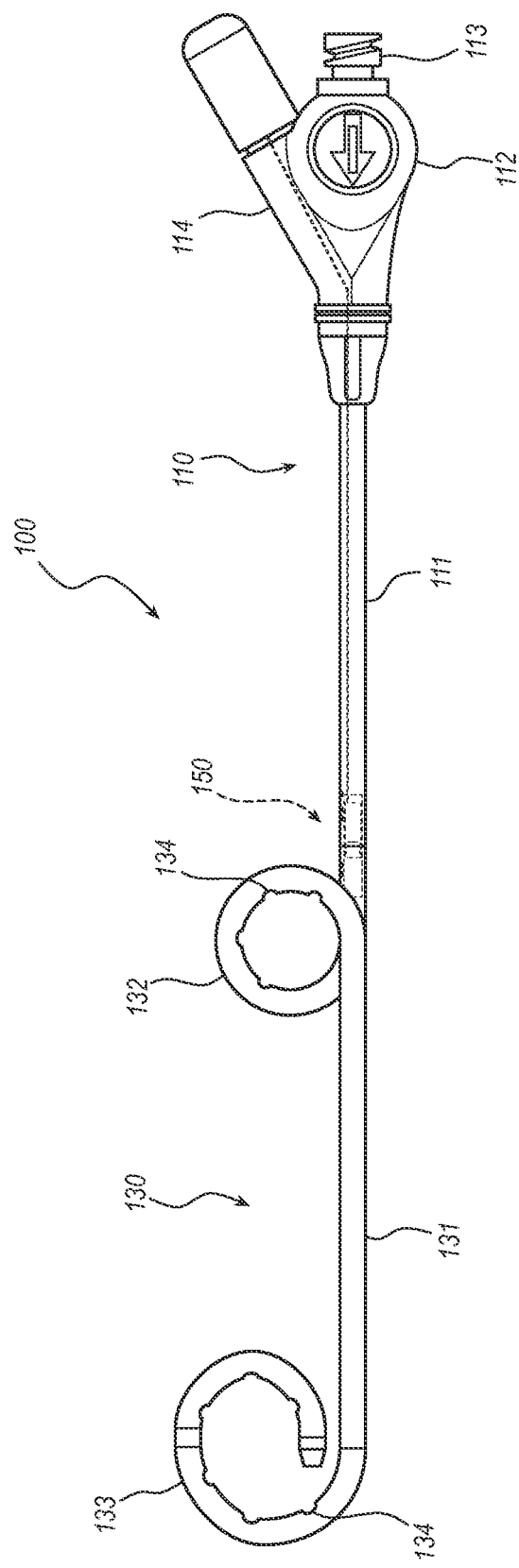
FIG. 1 is a side view of a drainage stent delivery system.

Drainage stents can be used to drain fluid from various cavities and/or organs within a patient. In certain instances, a drainage stent is a medical device used within a patient population that experience one or more complications associated with the urinary system, including the kidneys, ureters, and/or bladder. In some instances, complications may affect urinary flow and how these organs handle this function. These complications range from decreased urine flow to swelling of the kidneys or bladder. Many of these conditions are adversely impacted by the formation of kidney stones. To alleviate urinary system complications, a drainage stent delivery system may be used to deliver a ureteral stent to within the bladder, one or both of the kidneys, and/or one or both of the ureters.

The drainage stent delivery system can include a catheter body, a drainage stent member, and a coupling member. The coupling member is configured to selectively couple and decouple the drainage stent member from the catheter body. The coupling member is also configured to facilitate rotation of the catheter body and the stent member in a 1:1 ratio, such as while the system is being delivered into a patient. In other words, when coupled, the catheter body and the stent member can be rotationally fixed. In certain embodiments, the coupling member can include a first or proximal connector coupled to a distal end of the catheter body, a distal or second connector coupled to a proximal end of the stent member, and a telescoping connector slidably coupled to the first and second connectors. The first connector includes a tab configured to be received by a slot of the second connector. The telescoping connector displaces the tab radially outward to be disposed within the slot when the catheter body and the stent member are coupled together. To decouple the stent member from the catheter body, the telescoping connector is retracted from the first and second connectors, the tab is biased radially inward to displace the tab from the slot, and the catheter body and the stent member can be separated.

In an exemplary use, the drainage stent delivery system can be percutaneously inserted into a patient's body such that a distal end of the drainage stent is positioned within the patient's bladder and the proximal end is positioned within the patient's kidney. A body of the stent member can be disposed in the patient's ureter between the kidney and the bladder. The stent member can be used to drain the kidney when there is a blockage or restriction of the ureter. Following a period of time, for example two weeks, to allow stabilization of the stent member, the catheter body may be remotely decoupled from the stent member, by retracting a cable coupled to the telescoping connector, and removed from the patient without surgical intervention. In some embodiments, the stent member may include retention features, for example pigtails, at the proximal and distal ends.

In other applications, the drainage stent delivery system may be used to drain bile from the patient's liver or gall bladder into the patient's small intestine, where the stent member is disposed within a blocked or restricted bile duct. In still other applications, the drainage stent delivery system may be used to drain any suitable organ of the patient where a natural drainage tube or duct is blocked or restricted. For example, the drainage stent delivery system may be used to drain fluid from a patient's cranial cavity, pericardial cavity, pleural cavity, etc.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the drainage stent delivery system, the proximal end of the system refers to the end that extends from the patient's body and the distal end refers to the opposite end, the end disposed within the patient's organ to be drained. For example, the patient's bladder. Thus, if at one or more points in a procedure the practitioner changes the orientation of the system, as used herein, the term "proximal end" always refers to the end of the system extending from the patient's body (even if the distal end is temporarily closer to the practitioner).

"Fluid" is used in its broadest sense, to refer to any fluid, including both liquids and gases as well as solutions, compounds, suspensions, etc., which generally behave as fluids.

FIGS. 1-6 illustrate different views of drainage stent delivery systems and related components. In certain views each system may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-5B depict one embodiment of a drainage stent delivery system 100. In the illustrated embodiment of FIG. 1, the drainage stent delivery system 100 is partially composed of a catheter body 110, a stent member 130, and a coupling member 150. The stent member 130 is configured to facilitate drainage of a cavity of an organ of a patient. For example, the stent member 130 of the illustrated embodiment can be configured to provide a drainage channel from a patient's kidney to the patient's bladder when the patient's ureter is blocked or restricted.

As further depicted in the embodiment of FIG. 1, the catheter body 110 includes an elongate tubular member 111. A bifurcated hub 112 is coupled to a proximal end of the tubular member 111. The hub 112 can include a central port 113 and a side port 114. In other embodiments, the hub 112 may include three, four, or more ports. The central port 113 is in fluid communication with a lumen of the tubular member 111 and is configured for passage of an elongate medical instrument (e.g., guidewire) used to insert the drainage stent delivery system 100 into a patient. Additionally, the central port 113 can be used to deliver fluid into the patient and/or to drain fluid from the patient (e.g., urine from a kidney and/or bladder). The tubular member 111 may be formed from any suitable material. For example, the tubular member 111 can be formed from polymeric materials, including, but not limited to, polyurethane, polyethylene, polypropylene, nylon, etc. In other embodiments, the tubular member 111 may include a composite wall structure including a polymeric material as previously mentioned and a metal or fiber braid imbedded into the polymeric material. In yet another embodiment, the tubular member 111 may include an inner layer of a material configured to aid drainage of fluid through the tubular member 111 and/or increase lubricity of an inner surface of the tubular member 111. An outer layer may be of the same material as the inner layer. A length of the tubular member 111 may range from about 20 cm to about 100 cm, and an outer diameter may range from about 6 Fr to about 16 Fr. Other sizes are also contemplated. In some embodiments, the tubular member 111 can include a radiopaque agent or radiopaque bands to facilitate visualization and positioning of the tubular member 111 within the patient.

In the depicted embodiment of FIG. 1, the stent member 130 includes a tubular body 131. The tubular body 131 may be formed from any suitable material. For example, the tubular body 131 can be formed from polymeric materials, including, but not limited to, polyurethane, polyethylene, polypropylene, nylon, etc. In other embodiments, the tubular body 131 may include a composite wall structure including a polymeric material as previously mentioned and a metal or fiber braid imbedded into the polymeric material. In yet another embodiment, the tubular body 131 may include an inner layer of a material configured to aid drainage of fluid through the tubular body 131 and/or increase lubricity of an inner surface of the tubular body 131. An outer layer may be of the same material as the inner layer. A length of the tubular body 131 may range from about 20 cm to about 120 cm, and an outer diameter may range from about 6 Fr to about 16 Fr. Other sizes are also contemplated. In some embodiments, the tubular body 131 can include a radiopaque agent or bands to facilitate visualization and positioning of the tubular body 131 within the patient.

When the stent member 130 is in an unrestricted state, as shown in FIG. 1, the tubular body 131 includes a proximal retention member 132 and a distal retention member 133. For example, the retention members 132, 133 may be shaped as loops or pigtails disposed adjacent proximal and distal ends of the tubular body 131. In other embodiments, the retention members 132, 133 may be in the form of other expandable features, such as balloons, wings, bulges, etc. In the depicted embodiment, the retention members 132, 133 may be pre-formed, using heat, in the shape of loops or pigtails such that when the guidewire is removed from the stent member 130 during the insertion procedure, the retention members 132, 133 automatically transition from a straightened state to the unrestricted state shown in FIG. 1. In other embodiments, one or more of the retention members 132, 133 may include a shape memory insert (e.g., a metal or metal alloy) configured to transition the retention members 132, 133 from the straightened state to the unrestricted state. In still other embodiments, a tether (e.g., suture) may be releasably coupled to the proximal retention member 132 and/or the distal retention member 133 to facilitate transitioning of the proximal retention member 132 and/or the distal retention member 133 from the straightened state to the unrestricted state. Additionally, the tether can retain the retention members 132, 133 in the unrestricted state when the stent member 130 is coupled to the catheter body 110. In the depicted embodiment, the stent member 130 also includes a plurality of drainage ports 134 disposed adjacent the retention members 132, 133.

Figure 2:
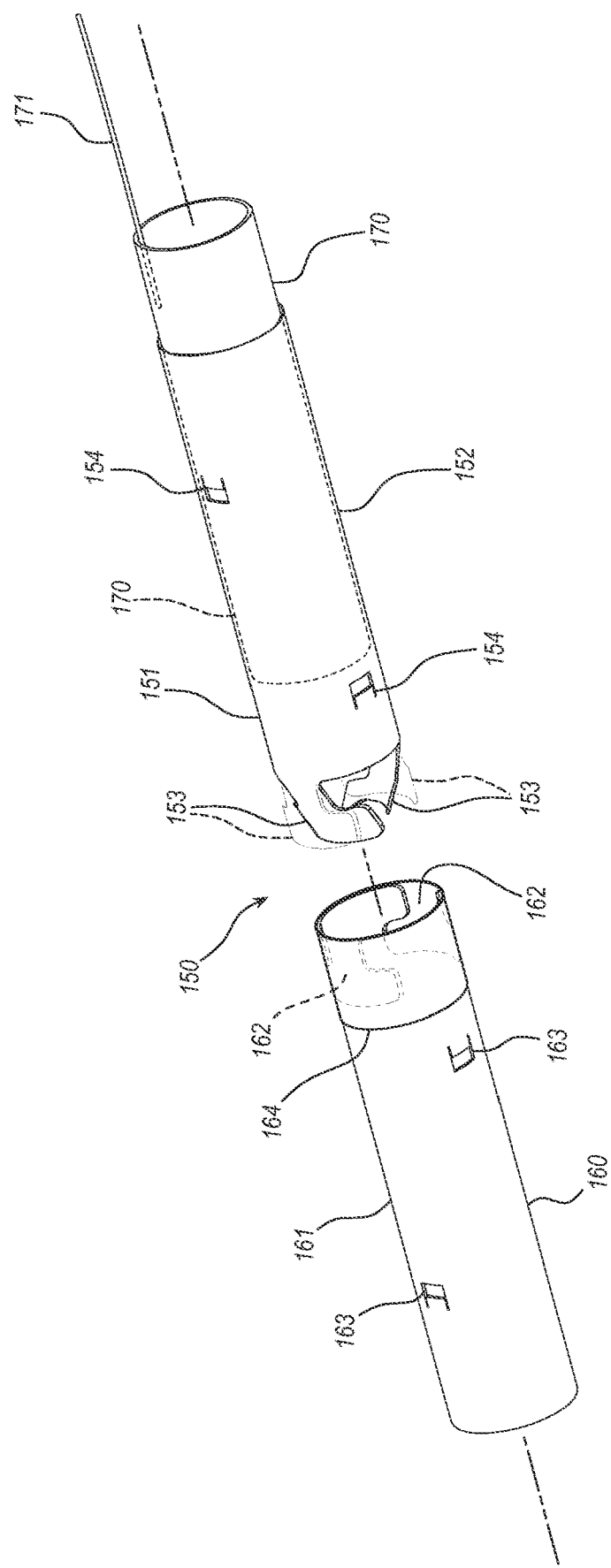
FIG. 2 is a perspective view of a coupling member of the drainage stent delivery system of FIG. 1.

As depicted in the embodiment of FIG. 1, the coupling member 150 selectively couples a distal end of the catheter body 110 to a proximal end of the stent member 130. As illustrated in FIG. 2, the coupling member 150 includes a first or proximal connector 151, a second or distal connector 160, and a telescoping connector 170. The first connector 151, as depicted in FIG. 2, includes a body 152 and a tab 153. The body 152 may be a hollow cylinder and may be formed from shape memory metals or metal alloys, such as nickel titanium alloy, copper aluminum nickel alloy, iron manganese silicon alloy, copper zinc aluminum alloy, etc. The body 152 may include at least one barb 154 extending radially outward from the body 152. A free-end of the barb 154 is directed distally such that the barb 154 can engage with an internal surface of the tubular member 111 of the catheter body 110 when the first connector 151 is disposed within the distal end of the tubular member 111. When the barb 154 is engaged, distal displacement of the first connector 151 from the tubular member 111 may be prevented. Optionally and/or alternatively, the body 152 may additionally include at least one barb 155 wherein a free-end of the barb 155 is directed proximally to prevent proximal displacement of the first connector 151 relative to the tubular member 111.

The tab 153 is shown to extend from a distal end of the first connector 151. In the illustrated embodiment, the first connector 151 includes two tabs 153 disposed circumferentially 180 degrees from each other. In other embodiments, the first connector 151 may include a single tab 153. In another embodiment, the first connector 151 may include three, four, five, or more tabs 153. The tab 153 is in a shape of a "T" with a cross portion disposed at a distal end of a longitudinal elongate portion. In other embodiments, the tab 153 may be of any suitable shape where a distal portion of the tab 153 is larger than a proximal portion. For example, the distal portion of the tab 153 may have a circular, oval, elliptical, triangular, square, polygonal, shape, etc. In a natural state, the tab 153 may be biased radially inward as depicted in FIG. 2.

As illustrated in FIG. 2, the second connector 160 includes a body 161 and a slot or receiver 162. The body 161 may be a hollow cylinder and may be formed from any suitable material such as metallic materials, including, but not limited to, stainless steel, titanium, and shape memory metals or metal alloys, such as nickel titanium alloy, copper aluminum nickel alloy, iron manganese silicon alloy, copper zinc aluminum alloy, etc. The body 161 may include at least one barb 163 extending radially outward from the body 161. A free-end of the barb 163 is directed proximally such that the barb 163 can engage with an internal surface of the tubular body 131 of the stent member 130 when the second connector 160 is disposed within the proximal end of the tubular body 131. When the barb 163 is engaged, proximal displacement of the second connector 160 from the tubular body 131 may be prevented. Optionally and/or alternatively, the body 161 may additionally include at least one barb 165 wherein a free-end of the barb 165 is directed distally to prevent distal displacement of the second connector 160 relative to the tubular member 131.

The slot 162 is shown disposed in a proximal end of the body 161. The illustrated embodiment of FIG. 2 shows two slots 162 disposed circumferentially 180 degrees apart. In another embodiment, the second connector 160 may include a single slot 162. In other embodiments, the second connector 160 may include three, four, five, or more slots 162. Stated another way, the number of slots 162 may equal the number of tabs 153 of the first connector 151, or vice versa. The slot 162 is shaped and sized to receive the tab 153 when the first connector 151 is coupled to the second connector 160. For example, in the illustrated embodiment of FIG. 2, the slot 162 is "T" shaped with a cross portion disposed distally of a longitudinal elongate portion. A sleeve 164 is shown disposed over the slot 162. The sleeve 164 can prevent the tab 153 from being displaced radially outward from the slot 162 when the connectors 151, 160 are coupled together.

The telescoping connector 170 can be disposed within bores or lumens of the first connector 151 and the second connector 160. The telescoping connector 170 can be a hollow cylinder made from any suitable material, such as metallic materials, including, but not limited to, stainless steel, titanium, and shape memory metals or metal alloys, such as nickel titanium alloy, copper aluminum nickel alloy, iron manganese silicon alloy, copper zinc aluminum alloy, etc. An outer diameter of the telescoping connector 170 is smaller than inner diameters of the bores of the first and second connectors 151, 160 to facilitate disposing of the telescoping connector 170 within the bores when the first and second connectors 151, 160 are coupled together and retraction of the telescoping connector 170 from the first and second connectors 151, 160 to enable decoupling of the first and second connectors 151, 160 from one another. An elongate cable 171 is coupled to the telescoping connector 170 to facilitate retraction of the telescoping connector 170 from the first and second connectors 151, 160. Various types of elongate cables 171 can be used. In some embodiments, the elongate cable 171 comprises a plurality of strands wound together.

Figure 6:
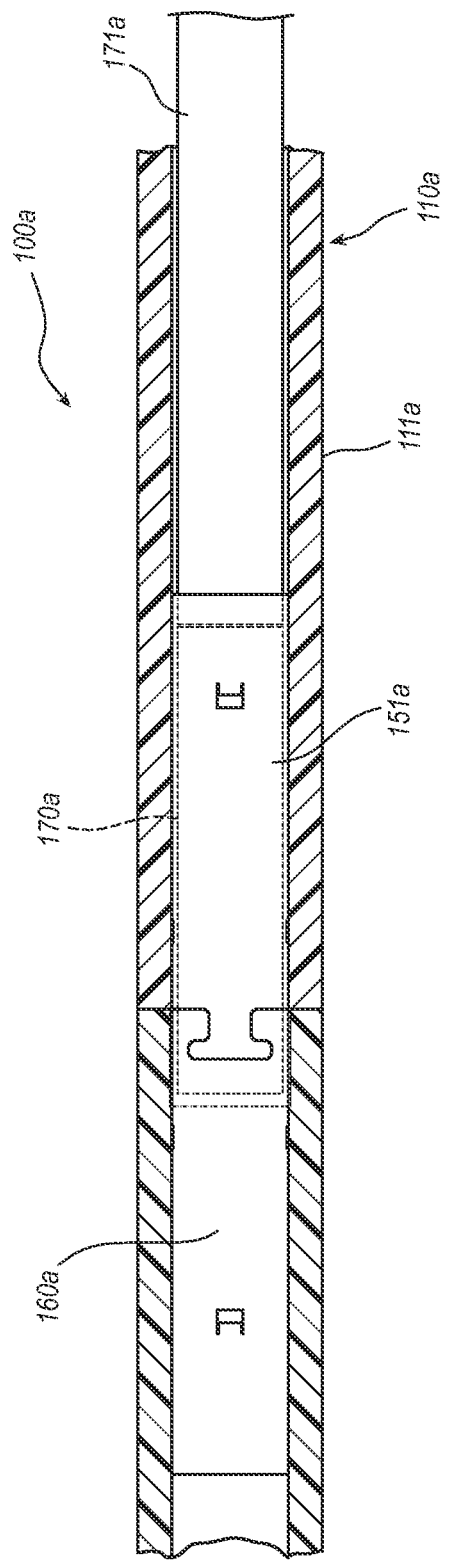
FIG. 6 is a partial cutaway side view of another drainage stent delivery system.

In another embodiment of a drainage stent delivery system 100a, as depicted in FIG. 6, an elongate cable 171a may be configured as an elongate tube circumferentially coupled to a proximal end of a telescoping connector 170a. The elongate cable 171a may be formed of any suitable material, such as metals or plastics, and can be coupled to the telescoping connector 170a using any suitable method, such as welding, brazing, bonding, etc. When tension is applied to the elongate cable 171a to retract the telescoping connector 170a from first and second connectors 151a, 160a, the elongate cable 171a is configured to apply a uniform, circumferential tension force to the telescoping connector 170a. This configuration may facilitate a linear displacement of the telescoping connector 170a from the first and second connectors 151a, 160a and provide a constant diameter through the tubular member 111a of the catheter body 110a.

Figure 3A:
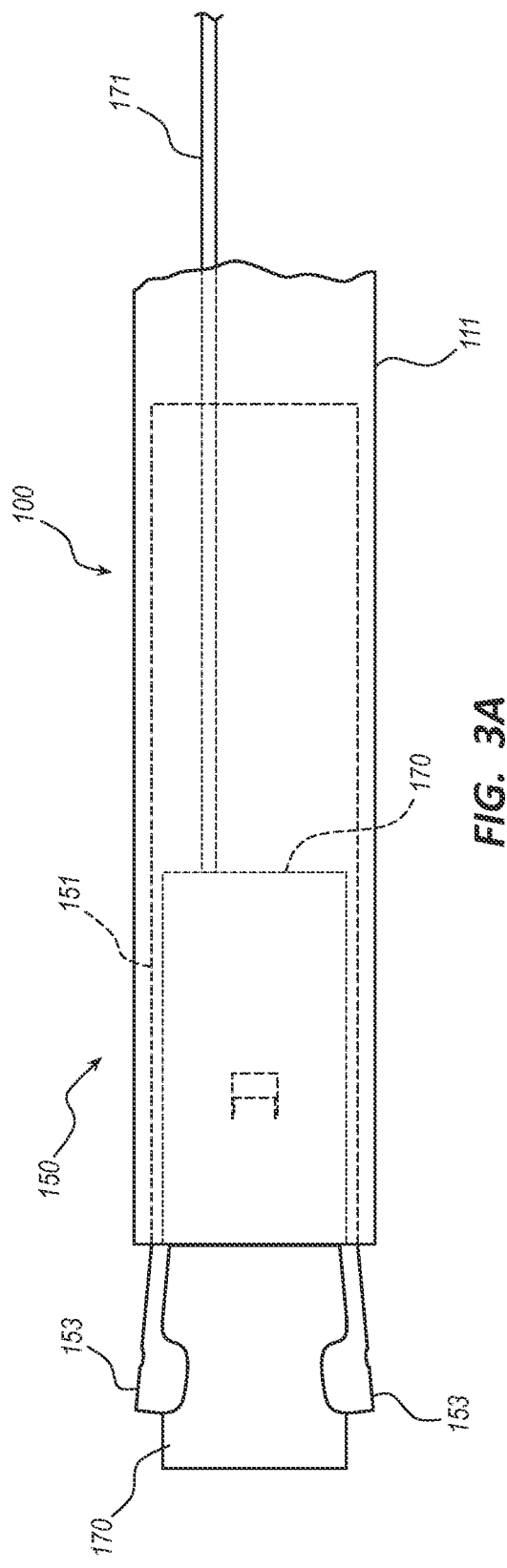
FIG. 3A is a side view of a portion of the coupling member of FIG. 2 with a tab in a radially outward distended configuration.
Figure 3B:
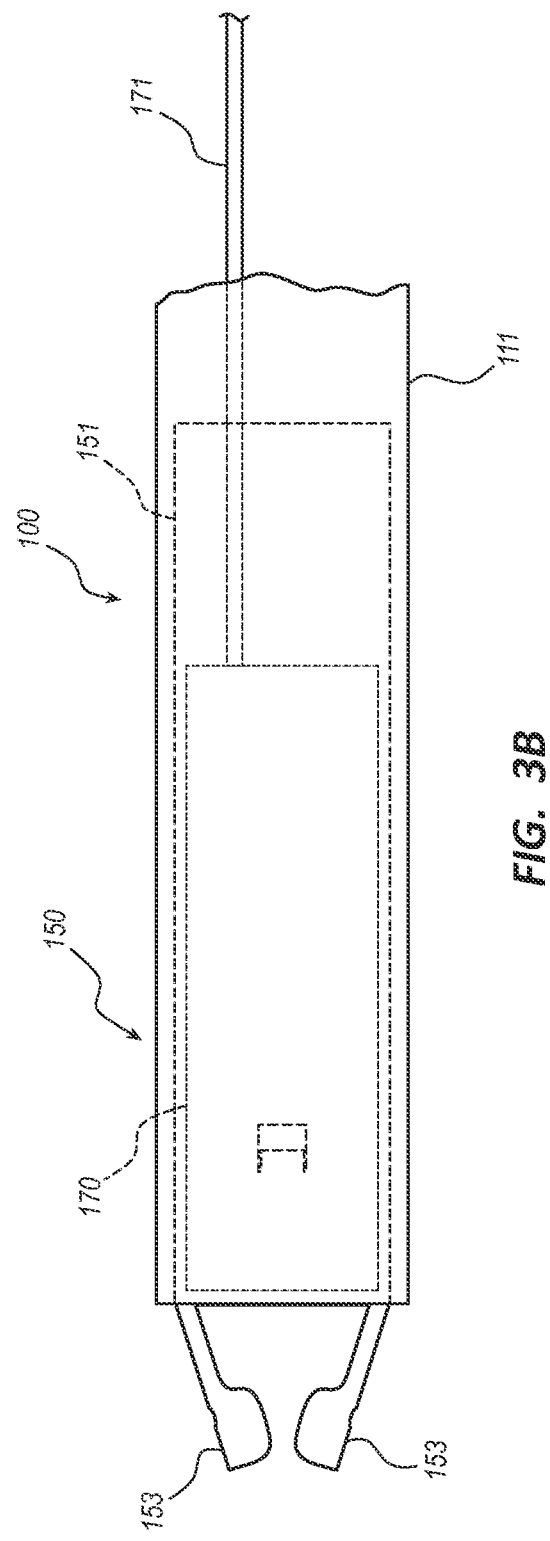
FIG. 3B is a side view of a portion of the coupling member of FIG. 2 with the tab in a biased radially inward configuration.

The telescoping connector 170 can be configured to displace the tab 153 radially outward, as shown in FIG. 3A, when the telescoping connector 170 is disposed through the bore of the first connector 151. This displacement allows the tab 153 to be selectively received by the slot 162 when the first and second connectors 151, 160 are coupled. As depicted in FIG. 3B, when the telescoping connector 170 is displaced proximally relative to the tab 153, the tab 153 biases radially inward. This biasing allows the tab 153 to be displaced from the slot 162 and the first and second connectors 151, 160 to decouple.

FIGS. 4A and 5A depict a portion of the drainage stent delivery system 100 in a coupled configuration, and FIGS. 4B and 5B depict the portion of the drainage stent delivery system 100 in a decoupled configuration. As shown in FIGS. 4A and 5A, the first connector 151 is disposed within the distal end of the tubular member 111 of the catheter body 110. The barb 154 of the first connector 151 can be engaging the surface of the lumen of the tubular member 111 to prevent distal displacement of the first connector 151. The tab 153 is displaced radially outward by the telescoping connector 170 and received into the slot 162 of the second connector 160. The telescoping connector 170 is disposed within the bores of the first and second connectors 151, 160 and is displacing the tab 153 radially outward. The cable 171 extends proximally from the telescoping connector 170. The second connector 160 is disposed within the proximal end of the lumen of the tubular body 131 of the stent member 130. The barb 163 can be engaging the inner wall surface of the tubular body 131 to prevent proximal displacement of the second connector 160. The sleeve 164 is disposed over the slot 162 to prevent the tab 153 from being displaced radially outward from the slot 162.

When in the coupled configuration, the lumens of the tubular member 111 and the tubular body 131 are aligned by the coupling member 150. Additionally, rotation of the catheter body 110 to position the stent member 130 within the patient's body can cause an equal rotation of the stent member 130. In other words, the catheter body 110 and the stent member 130 can be rotated at a 1:1 ratio as the drainage stent delivery system 100 is inserted into the patient's body. For instance, the tab 153 can engage the slot 162 to rotate the stent member 130 as the catheter body 110 is rotated. When coupled, the stent member 130 and catheter 110 can be described as being rotationally fixed.

As shown in FIGS. 4B and 5B, when the drainage stent delivery system 100 is in the decoupled configuration, the first connector 151 is disposed within the distal end of the tubular member 111 of the catheter body 110. The barb 154 of the first connector 151 can be engaging the surface of the lumen of the tubular member 111 to prevent distal displacement of the first connector 151. The second connector 160 is disposed within the proximal end of the lumen of the tubular body 131 of the stent member 130. The barb 163 is engaging the inner wall surface of the tubular body 131 to prevent proximal displacement of the second connector 160. The telescoping connector 170 is displaced proximally when tension is applied to the cable 171 such that the telescoping connector 170 is not disposed within the second connector 160. This allows the tab 153 to bias radially inward out of the slot 162 of the second connector 160.

The drainage stent delivery system 100 may be utilized to drain urine from the patient's kidney into the bladder when the patient's ureter is blocked or restricted. In some embodiments, the drainage stent delivery system may be used to drain bile from the patient's liver or gall bladder into the patient's small intestine, where the stent member is disposed within a blocked or restricted bile duct. In other embodiments, the drainage stent delivery system 100 may be utilized to drain any suitable body cavity, such as the cranial cavity, the pericardial cavity, the pleural cavity, etc.

An exemplary use of a drainage stent delivery system is to drain urine from the patient's kidney into the bladder when the patient's ureter is blocked or restricted. The drainage stent delivery system may be inserted into the patient over a previously inserted guidewire. A distal portion of the stent may be positioned in the bladder and a proximal portion positioned in the kidney. A body of the stent member can be disposed within a blocked or restricted ureter. Positioning of the stent member may require rotation of the stent member. A coupling member that selectively couples the stent member and a catheter body together can facilitate equal rotation of the catheter body and the stent member. The coupling member may include a proximal connector having a tab, a distal connector having a slot to receive the tab, and a telescoping connector removably disposed within the proximal and distal connectors. The telescoping connector can displace the tab radially outward and into the slot. Upon removal of the guidewire, retention members, such as pigtails, of the proximal and distal portions of the stent may form (automatically or manually) to retain the distal portion in the bladder and the proximal portion within the kidney.

A proximal portion of the catheter body can extend outside of the patient's body. A fluid drainage container may be coupled to a hub of the catheter body to collect the urine drained from the kidney and/or bladder. The drainage stent delivery system may remain indwelling for a period of time ranging from about one week to about three weeks. The catheter body may be decoupled from the stent member by proximally retracting the telescoping connector from the first and second connectors. For example, the telescoping connector can be retracted by a proximally directed force applied to a cable coupled to the telescoping connector. Upon retraction of the telescoping connector, the tab is biased radially inward and displaced from the slot. The catheter body is separated from the stent member and the catheter body is removed from the patient, leaving the stent member in place.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A stent delivery system comprising:
a catheter body having an inner lumen, a proximal end, and a distal end;
a stent member having an inner lumen and a proximal end; and
a coupling member comprising:
a first connector with an inner lumen, disposed within the inner lumen of the catheter body and at the distal end of the catheter body;
a second connector with an inner lumen, disposed within the inner lumen of the stent member and at the proximal end of the stent member; and
a telescoping connector slidingly coupled to the first connector and the second connector,
wherein coupling of the first connector to the second connector concentrically aligns the catheter body and the stent member and releasably secures the stent member to the catheter body, and
wherein retraction of the telescoping connector from the second connector releases the stent member from the catheter body, and wherein prior to retraction, the telescoping connector is constrained within the inner lumen of the catheter body and within the inner lumen of the second connector.

2. The stent delivery system of claim 1, wherein rotation of the catheter body causes equal rotation of the stent member when the first connector is coupled to the second connector.

3. The stent delivery system of claim 1, wherein the first connector comprises:
a lumen and a distal end;
a tab extending from the distal end; and
a barb extending radially outward from the body of the first connector,
wherein the barb engages with the catheter body to restrict distal displacement of the first connector.

4. The stent delivery system of claim 3, wherein the second connector comprises:
a lumen and a proximal end;
a slot in the proximal end; and
a barb extending radially outward from a body of the second connector,
wherein the barb engages with the stent member to restrict proximal displacement of the second connector.

5. The stent delivery system of claim 4, wherein the tab comprises a shape having an enlarged distal end, wherein the slot comprises a shape configured to receive the tab, and wherein the tab is biased radially inward in a natural configuration.

6. The stent delivery system of claim 4, wherein the tab is displace radially outward by the telescoping connector and is disposed within the slot of the second connector when the stent delivery system is in a coupled configuration.

7. The stent delivery system of claim 1, further comprising a cable coupled to the telescoping connector.

8. A stent delivery system comprising:
a catheter body having an inner lumen, a proximal end, and a distal end;
a stent member having an inner lumen and a proximal end; and
a coupling member comprising:
a first connector disposed within the inner lumen of the catheter body and at the distal end of the catheter body;
a second connector with an inner lumen disposed within the inner lumen of the stent member and at the proximal end of the stent member,
wherein a proximal end of the second connector is concentrically aligned with the inner lumen of the stent member; and
a telescoping connector slidingly coupled to the first connector and the second connector,
wherein coupling of the first connector to the second connector concentrically aligns the catheter body and the stent member and releasably secures the stent member to the catheter body, and
wherein retraction of the telescoping connector from the second connector releases the stent member from the catheter body.

9. The stent delivery system of claim 8, wherein rotation of the catheter body causes equal rotation of the stent member when the first connector is coupled to the second connector.

10. The stent delivery system of claim 8, wherein the first connector comprises:
a lumen and a distal end
a tab extending from the distal end; and
a barb extending radially outward from the body of the first connector,
wherein the barb engages with the catheter body to restrict distal displacement of the first connector.

11. The stent delivery system of claim 10, wherein the second connector comprises:
a lumen and a proximal end;
a slot in the proximal end; and
a barb extending radially outward from a body of the second connector,
wherein the barb engages with the stent member to restrict proximal displacement of the second connector.

12. The stent delivery system of claim 11, wherein the tab comprises a shape having an enlarged distal end, wherein the slot comprises a shape configured to receive the tab, and wherein the tab is biased radially inward in a natural configuration.

13. The stent delivery system of claim 11, wherein the tab is displace radially outward by the telescoping connector and is disposed within the slot of the second connector when the stent delivery system is in a coupled configuration.

14. The stent delivery system of claim 8, further comprising a cable coupled to the telescoping connector.

* * * * *